United States Patent
Desain et al.

(10) Patent No.: US 10,314,508 B2
(45) Date of Patent: Jun. 11, 2019

(54) BRAIN COMPUTER INTERFACE USING BROADBAND EVOKED POTENTIALS

(71) Applicant: Stichting Katholieke Universiteit, Nijmegen (NL)

(72) Inventors: Petrus Wilhelmus Maria Desain, Nijmegen (NL); Jordy Thielen, Nijmegen (NL); Philip Leonardus Cornelis van den Broek, Nijmegen (NL); Jason David Robert Farquhar, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 311 days.

(21) Appl. No.: 15/328,083

(22) PCT Filed: Jul. 20, 2015

(86) PCT No.: PCT/EP2015/066524
§ 371 (c)(1),
(2) Date: Jan. 23, 2017

(87) PCT Pub. No.: WO2016/012390
PCT Pub. Date: Jan. 28, 2016

(65) Prior Publication Data
US 2017/0202476 A1 Jul. 20, 2017

(30) Foreign Application Priority Data
Jul. 24, 2014 (NL) .................................. 2013245

(51) Int. Cl.
*A61B 5/0484* (2006.01)
*G06F 3/01* (2006.01)
(Continued)

(52) U.S. Cl.
CPC .......... *A61B 5/0484* (2013.01); *A61B 5/0042* (2013.01); *A61B 5/0075* (2013.01);
(Continued)

(58) Field of Classification Search
CPC . A61B 5/0484; A61B 5/0075; A61B 5/04009; A61B 5/04014; A61B 5/7203;
(Continued)

(56) References Cited

U.S. PATENT DOCUMENTS 5,692,517 A * 12/1997 Junker ................. A61B 5/0482
600/545
6,349,231 B1 * 2/2002 Musha ................. A61B 5/0482
600/544
(Continued)

FOREIGN PATENT DOCUMENTS

WO 2010008276 A1 1/2010

OTHER PUBLICATIONS

Guangyu Bin et al: A high-speed BCI based on code modulation VEP, Journal of Neural Engineering, Institute of Physics Publishing, Bristol, GB, Published Mar. 24, 2011, XP020189275.
(Continued)

*Primary Examiner* — Eric F Winakur
(74) *Attorney, Agent, or Firm* — N.V. Nederlandsch Octrooibureau; Catherine A. Shultz; Tamara C. Stegmann (57) ABSTRACT

Method for processing a brain wave signal (4) obtained from a person using a brain wave detector (5). One or more stimuli are applied to the person in which each of the one or more stimuli comprises a pseudo random noise component modulating the stimulus intensity. A brain wave signal (4) is detected after applying the one or more stimuli. The detected brain wave signal is processed to calculate which of the one or more stimuli is present in the detected brain wave signal using correlation techniques. The pseudo random noise component comprises a pseudo random noise sequence of the class of maximum length sequences, which are further modulated with twice their associated bit frequency.

13 Claims, 5 Drawing Sheets

(51) Int. Cl.
*A61B 5/048* (2006.01)
*A61B 5/00* (2006.01)
*A61B 5/04* (2006.01)
*A61B 5/055* (2006.01)

(52) U.S. Cl.
CPC .......... *A61B 5/048* (2013.01); *A61B 5/04009* (2013.01); *A61B 5/04014* (2013.01); *A61B 5/7203* (2013.01); *A61B 5/7246* (2013.01); *A61B 5/7264* (2013.01); *G06F 3/015* (2013.01); *A61B 5/055* (2013.01); *A61B 5/7267* (2013.01); *A61B 2576/026* (2013.01)

(58) Field of Classification Search
CPC ..... A61B 5/7246; A61B 5/7264; A61B 5/048; A61B 5/0042; G06F 3/015
See application file for complete search history.

(56) References Cited

U.S. PATENT DOCUMENTS

| | | | | |
|---|---|---|---|---|
| 7,349,727 B2* | 3/2008 | Obata | ................ | A61B 5/14553 600/310 |
| 7,729,732 B2* | 6/2010 | Ohashi | ............... | A61B 5/14553 600/310 |
| 2011/0251511 A1* | 10/2011 | Desain | ............... | A61B 5/04845 600/544 |
| 2014/0052016 A1* | 2/2014 | Cheng | ................. | A61B 5/0484 600/544 |

OTHER PUBLICATIONS

Masaki Nakanishi et al: "Periodicity detection for BCI based on periodic code modulation visual evoked potentials", 2012 IEEE International Conference on Acoustics, Speech and Signal Processing (ICASSP 2012) : Kyoto, Japan, Mar. 25-30, 2012, p. 665-668, XP032227215.

Keiko Momose: "Simultaneous detection method of P300 event-related potentials and eye gaze point using multi-pseudorandom and flash stimulation for brain computer interface", Engineering in Medicine and Biology Society, 2008. EMBS 2008. 30th Annual International Conference of the IEEE, IEEE, Piscataway, NJ, USA, Aug. 20, 2008 (Aug. 20, 2008), p. 666-669, XP031508041.

Guangyu Bin et al: "VEP-based brain-computer interfaces: time, frequency, and code modulations [Research Frontier]", IEEE Computational Intelligence Magazine, IEEE, US, Nov. 1, 2009 (Nov. 1, 2009), p. 22-26, XP011278918.

* cited by examiner

BRAIN COMPUTER INTERFACE USING BROADBAND EVOKED POTENTIALS

FIELD OF THE INVENTION

The present invention relates to brain computer interfacing using noise tagging. More in particular, the present invention relates to a method for processing a brain wave signal obtained from a person using a brain wave detector, comprising applying one or more stimuli to the person, in which each of the one or more stimuli comprises a pseudo random noise component modulating the stimulus intensity, detecting a brain wave signal after applying the one or more stimuli, and processing the detected brain wave signal to provide a prediction of which of the one or more stimuli is present in the detected brain wave signal using correlation techniques.

PRIOR ART

A brain computer interface solution is known from International patent publication WO2010/008276 of the same applicant as for the present application. This publication discloses a method and brain computer interface for processing a brain wave signal obtained from a person using a brain wave detector. One or more stimuli are applied to the person which each comprise a pseudo random noise component. A brain wave signal is detected and mental processing of the one or more stimuli is tracked by correlating the pseudo random noise component and the brain wave signal.

SUMMARY OF THE INVENTION

The present invention seeks to provide an improved method and system for a brain computer interface, which is more robust and more efficient, and easier to train.

According to the present invention, a method for processing a brain wave signal obtained from a person using a brain wave detector is provided, the method comprising:

applying one or more stimuli to the person in which each of the one or more stimuli comprises a pseudo random noise component modulating the stimulus intensity;

detecting a brain wave signal after applying the one or more stimuli; and processing the detected brain wave signal to calculate which of the one or more stimuli is present in the detected brain wave signal using correlation techniques, (and thus a measure of which stimuli are attended by the person/subject) wherein the pseudo random noise component comprises a pseudo random noise sequence of the class of maximum length sequences, which are further modulated with twice their associated bit frequency. This will result in removal of the low-frequency content in the detected signals, and restrict the spectral content to one octave band, allowing a more robust and reliable training and prediction in the brain computer interface method.

In an embodiment, the class of maximum length sequences comprise Gold code sequences. These can be obtained using a pair of maximum-length sequences, and will result in a bit sequence having a near-zero auto-correlation pattern for all non-zero delays.

In a further embodiment, the pseudo random noise component is one of an optimized set of pseudo random noise sequences, wherein the optimized set is obtained using cross correlation and auto correlation parameters of the associated predicted brain responses. This optimized set or subset of sequences exhibit the least pair-wise maximum cross-correlations, and is also indicated as the platinum pick.

The optimized set may be obtained in an embodiment by first clustering the set of pseudo random noise codes, and providing the optimized set by selecting one pseudo random noise sequence from each cluster. Furthermore, the optimized set may be provided using an iterative process, wherein each cluster is subsequently reduced to a single pseudo random noise sequence. This results in less parameters that need to be calculated in the remaining selection process.

In a spatial type of BCI implementation, e.g. a speller implementation, the pseudo random noise sequences of the optimized set are allocated to a position in a two-dimensional matrix, wherein cross-talk between neighboring cells in the two-dimensional matrix is minimized. This ensures that selection by a user of neighboring cells can be detected with the highest possible probability of success.

In a further embodiment, processing the detected brain wave signal comprises spatial filtering (e.g. Canonical Correlation Analysis, CCA) and classification by template matching. Furthermore, spatial filtering may be applied during training of a classifier to obtain a template filter and a trial filter.

In further embodiments, processing the detected brain wave signal comprises template matching with templates predicted by applying re-convolution processing. Re-convolution processing comprises first de-convolution calculations, and subsequently convolution calculations. As in the embodiment using Gold codes, the responses all comprise two pulse shapes (a short one and a long one), this processing is suitable to provide a reliable prediction. In a specific embodiment, the template prediction comprises using a response of a first fixed duration pulse and a response of second fixed duration pulse, which is the result of mixing with a double clock frequency to obtain the pseudo-random noise sequences of the present invention embodiments.

In a further embodiment, the one or more stimuli are applied continuously, allowing to implement an asynchronous BCI, wherein the detection part has no need of knowledge of the time synchronization of the stimuli.

In a further aspect, the present invention relates to a brain computer interface comprising a stimulator for applying stimuli to a person, a detector for obtaining a brain wave signal from the person, a processor connected to the detector and arranged to process the brain wave signal according to any one of the present invention method embodiments, and a device connected to the processor and arranged to receive processed data from the processor.

In an even further aspect, the present invention relates to a computer program product comprising computer executable code, which when loaded on a computer system connected to a stimulator for applying stimuli to a person and to a detector arranged to receive data associated with a brain wave signal, provides the computer system with the functionality of the method according to any one of the present invention method embodiments.

SHORT DESCRIPTION OF DRAWINGS

The present invention will be discussed in more detail below, using a number of exemplary embodiments, with reference to the attached drawings, in which.

DETAILED DESCRIPTION OF EXEMPLARY EMBODIMENTS

A Brain Computer Interface (BCI) is a system that enables users to control a device by using brain activity only. BCIs are implemented for many purposes, such as cursor-control, speller-devices, wheelchair-control, neural-rehabilitation, error-potential classification, gaming, and second language training.

Figure 1:
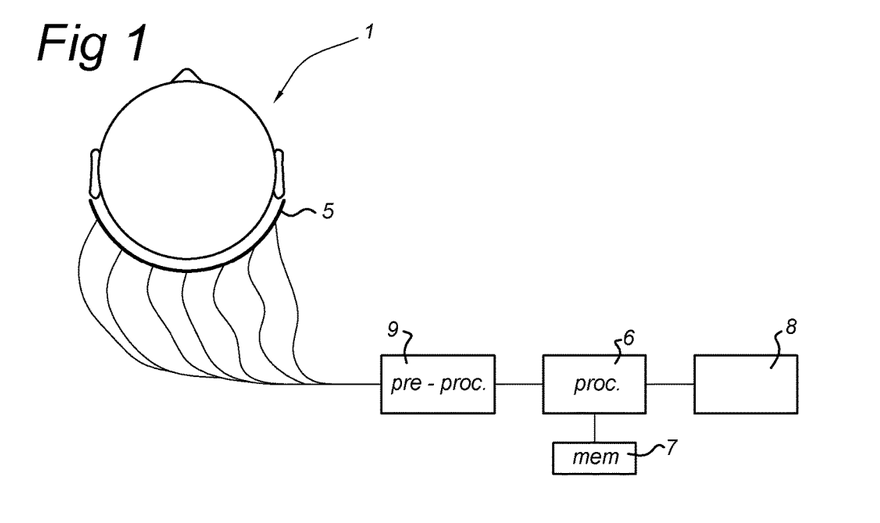
FIG. 1 shows a schematic view of a brain computer interface implementation according to an embodiment of the present invention.

In an exemplary embodiment of a detection system according to the present invention exploiting noise tagging, a detector 5 is positioned on the scalp of a test person or subject 1, as shown in the schematic view of FIG. 1. The detector 5 is used to obtain the brain wave signal representing brain activity using a pre-processor 9 which includes amplifiers, filters and/or analog to digital converters as known in the art for obtaining a brain wave signal. The brain wave signal representing brain activity of the subject 1 is one of possible measurement signals, such as but not limited to Electroencephalography (EEG), Magnetoencephalography (MEG), Near-infrared spectrometry (NIRS) or Magnetic resonance imaging (MRI) signal, each requiring a specific arrangement of the detector 5 (sensors, electrodes, etc.). In the present invention embodiments, brain activity may be evoked by visual, auditory or tactile stimuli, although many exemplary embodiments will be discussed in relation to visual stimuli only.

The brain wave signal is fed to a processor 6, such as a general-purpose computer, or a dedicated signal processor. The processor 6 is connected to a memory unit 7 (e.g. a hard disk) for storing intermediate data during signal processing and for storing instructions for the processor 6. Also, the processor 6 may be connected to a further apparatus 8, such as a display for showing the processing results, or a system or device to be controlled by the test person. E.g. this may be implemented as a Brain Computer Interface (BCI), in which control signals to a system or device 8 are generated based on the measured brain wave signal (e.g. by detecting to which of two stimuli the test person's attention is directed).

The processor 6 is arranged to perform any one of the method embodiments described using the proper input and output signals. The method embodiments may also be implemented as a computer program, e.g. stored on a computer program product such as an optical disc or on the memory unit 7, comprising computer executable code or instructions. When the computer program is loaded on a generally known computer system having the appropriate interfaces (i.e. connected to a stimulator for applying stimuli to a person and to a detector 5 arranged to receive data associated with a brain wave signal (e.g. via pre-processor 9)), the functionality of the method embodiments is obtained.

The present invention embodiments may be implemented as a brain computer interface (as hardware implementation) comprising a stimulator for applying stimuli to a person (see also block 3 in the embodiments described below), a detector 5 for obtaining a brain wave signal 4 from a person, a processor 6 connected to the detector 5 and arranged to process the brain wave signal 4 according to any one of the present invention method embodiments, and a device 7, 8 connected to the processor 6 and arranged to receive processed data from the processor 6.] Furthermore, the present invention may be embodied as a computer program product comprising computer executable code, which when loaded on a computer system arranged to receive data associated with a brain wave signal, provides the computer system with the functionality of the present invention method embodiments.

In a general BCI the information flow is cyclic and contains various stages. First there may be a certain perceptual stimulation while the user 1 performs a task. The stimulation and task together evoke specific brain activity that is related to the user's intention. This brain activity is measured using an appropriate means (e.g., EEG, fNIRS, MEG, fMRI). Usually the data has to be preprocessed (e.g., to remove artefacts), e.g. using the pro-processor as shown in FIG. 1. After that, the relevant features related to the task and stimuli have to be extracted, e.g. using the processor 6. A pre-trained classifier interprets these features by making a binary or multi-class decision. Often the output is presented to the user via an observable system 8 that may form new (feedback) stimulation. During this BCI cycle, the user will adapt (e.g., learn, habituate). Hence ideally the system has to adapt as well in this mutual dependency.

Still a main aim of research is how to improve BCI, as robustness and speed are often still a limiting factor for their application. In addition the ill-understood subject dependency, often expressed inappropriately as 'BCI-illiteracy', challenges current BCI research and deployment of its results.

The BCI speller is a well-studied output device for BCI. It allows one to communicate solely by using brain activity. A typical speller allows a user to select individual characters by eliciting specific brain activity. Research in this domain is especially of importance for patients with Amyotrophic Lateral Sclerosis (ALS). These patients are fully aware of their environment, though they cannot communicate or interact with it, because of a gradual decline of their motor abilities.

Fortunately, these patients have normal brain activity, which can be measured and used for communication by a speller BCI. Restoration of communication, or communication by brain activity only, can be enabled by a BCI speller application. The visual speller comprises a 6 by 6 grid that contains 36 characters. During stimulation the rows and columns are flashed sequentially, in a random order, evoking a specific brain response whenever the row or column of interest is flashed. A classifier can detect this difference to discriminate attended from unattended flashes. As each character has a unique flashing sequence, the attended character can be determined comparing the classifiers' predicted flash sequence with the character sequences. The detection of a number of flashes is integrated over time to yield a reliable classifier output. Recently, the random-sequence speller has been improved by optimizing the code-book of flashes using generative models. Another novel method is to use a checkerboard paradigm to drive the speller. Because ALS patients often loose the ability to control their gaze, the speller has been applied using different modalities like auditory and tactile. Another approach is to use covert visual attention so that usability does not rely on eye movement anymore.

One class of BCI operates by detecting selective attention. For that, a set of parallel visual, auditory or tactile stimuli is positioned at different locations and the subject's task is to attend to one of them, ignoring the others. The stimuli are usually not static but become distinguishable by their onset timing patterns or by modulations at a certain frequency: they are tagged or watermarked. Various markers can be detected from the Electroencephalogram (EEG), which indicate the attended stimulus. One of these is the P300, which signals the time of occurrence of an item of interest embedded in a random sequential presentation of a set of other items. Moreover, the P300 is more or less independent of modality of stimulation. However, using the P300 in a speller design is known to have its limits in terms of Information Transfer Rates (ITR) that can be achieved with it.

Another method of stimulation is by tagging each item with a different frequency. The attended item then results in a so called Steady State Evoked Potential (SSEP) at the same frequency, which is phase locked to the stimulation. These responses are generated at lower levels of perceptual processing and are considered to be more modality specific. They occur in covert attention but are much clearer when the stimulation can be modulated by overt behavior, like moving eye gaze. SSEPs for BCI have been well studied especially in the visual domain, and though they work well, the speed and reliability of SSEP-based BCI leaves much to be desired. One reason for this could be that the SSEP responses are swamped by spontaneous brain oscillations in the same 10-40 Hertz band. In addition the subject specific spectral sensitivity profile limits the generic applicability of SSEP-based BCI, which makes a fast plug-and-play approach not feasible. Furthermore, for BCIs that require many different classes, like a speller BCI, the separation between frequencies may become too narrow to be distinguished in a short time period (i.e., the spectral peaks in the responses starts to overlap). Still, in the visual domain, SSVEP-based BCI have proven to be successful, especially for BCIs that depend on directing gaze. The fastest SSVEP-based BCI transfers on average 68 bits per minute. For a speller this reflects a typing speed of about 12.2 characters per minute. This is much higher than the more common P300 speller, which often reaches no more than about 5 characters per minute.

In contrast to frequency tagging, noise tagging is a type of stimulus watermarking in which each stimulus is marked by a specific non-periodic pattern. These patterns are called noise tags, but they are only pseudo-random, as the specific noise-like pattern is known. There are studies that use a form of continuous noise, but most studies use bit-sequences. For these sometimes error-correcting codes are used, but often so-called pseudo-random noise codes are employed. The bit-sequences themselves are used to modulate the stimulus intensity (e.g., amplitude or luminance), as in frequency tagging. Noise tags cover a specific band of the frequency spectrum, whereas frequency tags exhibit a narrow peak, possibly repeated at its harmonics.

Noise tags elicit responses in the brain activity that are stimulus locked and appear as Broad Band Evoked Potentials (BBEP) in the measured brain wave signal. They can function as a marker for a specific stimulus. Pseudo-random noise codes are presented at a specific rate: the bit-clock. Every period of the bit-clock either a 1 or a 0 is generated. The pseudo-random bit-sequences are generated with a linear feedback shift register with a feedback of a combination (an exclusive-or operation, or equivalently a sum modulo 2) of some of its outputs to its input. Choosing specific taps yields sequences of a maximal duration before they repeat themselves. These so-called maximum length sequences or m-sequences have been used to watermark stimuli and have resulted into high ITR.

Yet, according to the present invention embodiments, a new paradigm is proposed for noise tagging with another family of pseudo-random bit-sequences. More specifically, instead of shifted versions of one m-sequence a set of Gold codes is generated in a specific embodiment. This is done by combining a preferential pair of m-sequences. The set of Gold codes is then modulated in such a way that specific properties are created that allow to model and predict the BBEP responses to them.

In general terms, in a first group of embodiments, a method is provided for processing a brain wave signal obtained from a person using a brain wave detector, comprising:

applying one or more stimuli to the person in which each of the one or more stimuli comprises a pseudo random noise component modulating the stimulus intensity;

detecting a brain wave signal after applying the one or more stimuli; and processing the detected brain wave signal to calculate which of the one or more stimuli is present in the detected brain wave signal using correlation techniques (i.e. a measure of which stimuli are attended by the person), wherein the pseudo random noise component comprises a pseudo random noise sequence of the class of maximum length sequences which are further modulated with twice their associated bit frequency.

Pseudo-random bit-sequences are codes that are generated in a deterministic way. However, apart from having a fixed (long) length after which they repeat themselves, they have properties of random bit-sequences. These bit-sequences can be generated by a linear feedback shift register of length m with any starting state (except all-zero) and an input that is fed back from an exclusive-or operator (modulo 2 addition) of a few specific taps of the register. For a given length of the register, specific tap patterns are known that guarantee the generation of a maximum length sequence (or m-sequence) that visits all $2^m-1$ possible states (except the all zero state, hence the minus 1). Therefore, the length of such a sequence equals $l=2^m-1$. Combining a so-called preferential pair of m-sequences by an exclusive or operation, one can generate bit-sequences that exhibit a near-zero auto-correlation pattern for all non-zero lags (named Gold codes). Thus a Gold code is not easily confused with a delayed version of itself. In a further embodiment of the present invention, this is implemented as the class of maximum length sequences comprising Gold code sequences.

Furthermore, by delaying one of the preferential m-sequences with a time lag t ($0 \leq t \leq n$) before combining it with the other, a whole family of $n=2^m+1$ Gold codes is generated (the two m-sequences themselves may be added to the set as well). The delay may alternatively be expressed as a different starting state (seed) of the shift register. The Gold codes of this family have near zero cross-correlation between them and thus are not easily confused with each other. Gold-codes retain some properties of m-sequences. First, they are nearly balanced (a full code contains one zero less than it contains ones). And second, on average they have a special run-length distribution in which the frequency of occurrence of a long run of the same symbol is inversely proportional to the length of that run. It is this property that gives m-sequences and Gold codes a very broad spectral content with quite some power in low frequencies. If Fc is the bit-clock, then the main spectrum extends from Fc/(n+1) to Fc with a 1/f fall-off above it, reflecting the steep square-wave-like character of the signal. An example of such a Gold code/m-sequence is shown in FIG. 2a.

When used as stimuli, the low-frequency part of the spectrum may extend below the perceptual fusion boundary where perceptual processes are fundamentally different. This may cause different responses because of different perceptual processing. In addition, low frequency stimulation may be more annoying (visual flicker or auditory stutter). Moreover, the long runs in the sequences are a problem for BCI because often large brain responses are triggered by transitions after longer resting states. To avoid these problems the pseudo-random noise codes are modulated with twice their bit clock (a kind of phase shift keying) in the present invention embodiments.

Figure 2A:
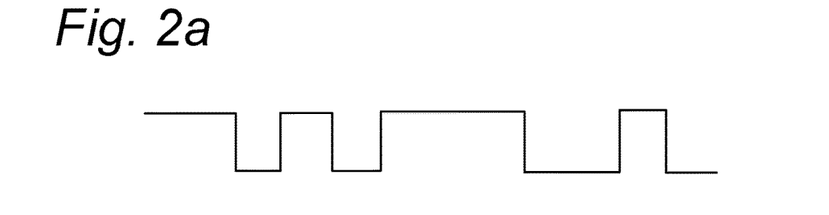
FIG. 2a-c show waveform diagrams as used in the present invention embodiments for modulating the Gold codes.
Figure 2B:
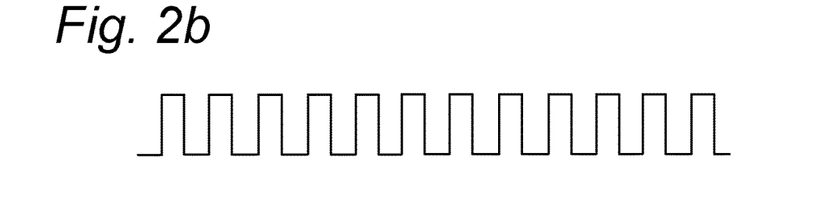
Figure 2C:
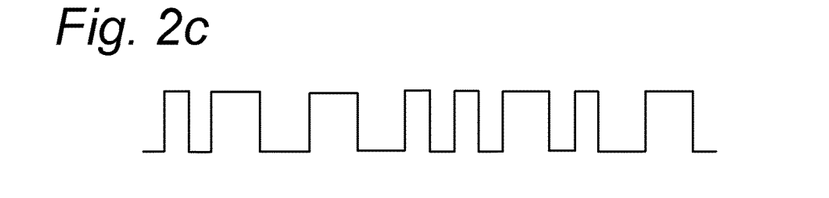
Figure 3:
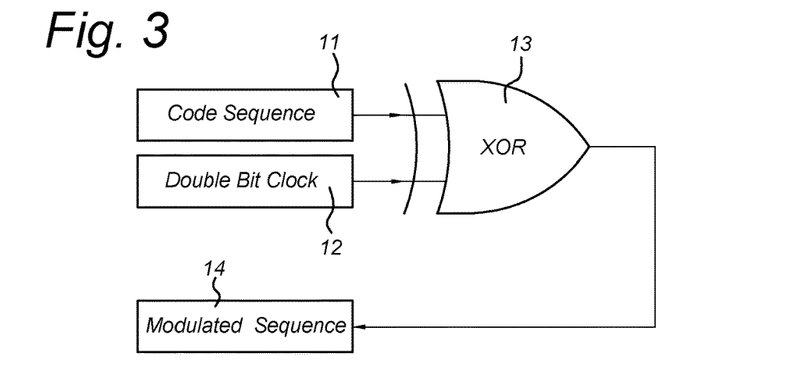
FIG. 3 shows a logical diagram implementing the generation of suitable pseudo-random noise sequences for the present invention methods.

This is shown schematically in FIG. 2a-c and FIG. 3. As mentioned, FIG. 2a shows an example of code sequence 11 in the form of a Gold code having a bit clock frequency Fc. The associated double bit clock signal 12 is shown in FIG. 2b. When inputting these two signals to an exclusive or gate 13, the resulting modulated sequence 14 is obtained, which is shown in FIG. 2c.

This restricts the broad spectral character to an octave band and removes low-frequency content. More specifically, this modulation has an advantage in the detection process as well as it effectively recodes the signal, replacing each bit by a transition. As every 1 is replaced by 10 and every 0 by 01 this yields a bit-sequence with only runs of one or two 1's or 0's.

The modulated bit-sequences 14 (modulated Gold codes) still exhibit the desirable auto- and cross-correlation properties. In addition, now all sequences are balanced and have only two runs (one-third of length 1, all others of length 2). The length of a modulated Gold Codes is $l=2*(2^m+1)$.

A code family of modulated Gold codes contains $n=2^m+1$ codes (given the shift register length m). In designing a BCI user interface sometimes only k codes (k≤n) are needed and there is freedom to pick a subset. Note that while the stimuli are all uncorrelated as binary signals, this does not entail that the responses to the stimuli are uncorrelated too. Thus the selection process aims at finding a subset of codes that yields responses that are most easily distinguished. This is achieved in further embodiments of the present invention by finding the responses that exhibit the least pair-wise maximum cross-correlations. The subset of sequences with the least correlating responses is indicated in the following as the Platinum subset. In more general wording, the pseudo random noise component is one of an optimized set of pseudo random noise sequences, wherein the optimized set is obtained using cross correlation and auto correlation parameters of the associated predicted brain responses.

By using re-convolution techniques (see also further below) it is possible to predict the responses to each code in the set of n modulated Gold codes, without collecting the real responses. Thus it becomes possible to calculate the full cross-correlation matrix of responses to all individual codes. However, choosing a subset of k codes with a minimal pair-wise maximal correlation between their responses by exhaustive search is prohibitive, unless k is close to 1 or n.

The combinatorial explosion is harnessed by using a two-step approach. First the likely candidates are selected by clustering and then select the best candidate from each cluster. The optimized set is thus obtained in a further embodiment by first clustering the set of pseudo random noise codes, and providing the optimized set by selecting one pseudo random noise sequence from each cluster.

Using hierarchical clustering (with single linkage) one can collect codes in groups where within-group correlation is minimized and between-group correlation is maximized. To yield a partition of codes the clustering-tree is trimmed at the level that yields k leaves. Choosing the best representative of each cluster is the remaining task, which is easier than the original problem.

In a further embodiment, a greedy algorithm is used that picks the representatives per cluster sequentially. At each step a cluster is selected and the codes' response from within that cluster that minimizes the maximum correlation with all responses of codes outside the cluster is chosen as representative. The cluster is then cropped to this one representative.

Hence subsequent iterations compare with a decreasing number of data points. This process is iterated until all groups comprise only one code: The data is clustered based upon hierarchical single-linkage clustering. A non-singleton cluster with the maximum correlation to a response in any other cluster is selected. The maximum distances of each inside-cluster points with all outside-cluster points are observed. The data point with maximum minimum distance is selected and all other within-cluster points are removed. This step is repeated for the next cluster, only considering 'living' points, until each cluster is expressed by a single representative. These form the optimal subset (or Platinum subset).

The above embodiments may also be described more generally, wherein the optimized set is provided using an iterative process, wherein each cluster is subsequently reduced to a single pseudo random noise sequence.

In the specific implementation of a visual speller BCI the stimuli are arranged in a 6 by 6 matrix of cells of a specific size, and the screen is positioned at a certain distance from the user. Depending on the angle of view, the pseudo-random noise codes used for neighboring graphical areas may 'leak through' and may be confused more easily. An optimal layout can allocate the codes in such a way that the highest correlating responses are not allocated to neighboring cells. For a 6 by 6 speller matrix, given an optimal subset of 36 codes out of the original set, the number of configurations is so large that an optimal layout cannot be selected exhaustively by enumeration. Instead a simulated annealing-like procedure is used to arrive at a near-optimal layout.

The algorithm starts with an arbitrary allocation of pseudo-random noise codes to matrix cells. Then sequentially the two worst neighboring codes are selected by means of largest pair wise correlation. The algorithm searches exhaustively for the best swap that gives the least maximum pair wise correlation between vertical, horizontal and diagonal neighbors.

The algorithm performs the swap and continues with finding the next worst neighbor, proceeding until the swap does not result into a better layout. This algorithm yields a near-optimal layout with allocation of codes to cells with low correlations between responses of neighboring cells. As global optimality is not guaranteed, the algorithm tries several initial random layouts in a further optional embodiment. The layout with the least maximal pair-wise cross correlation is selected.

Thus, a further embodiment relates to a method wherein the pseudo random noise sequences of the optimized set are allocated to a position in a two-dimensional matrix, wherein cross-talk between neighboring cells in the two-dimensional matrix is minimized.

The processing pipeline for detecting the BBEPs in the processing of the detected brain wave signal is quite elaborate. Four major processing steps may be identified, which are discussed in more detail below, i.e. spatial filtering (to reduce the quite noisy brain wave signal (e.g. in the case of EEG signals)); classification by template matching; template prediction; and early stopping.

In a group of embodiments of the present invention, processing the detected brain wave signal comprises spatial filtering (e.g. CCA, see below) and classification by template matching.

First, a method of spatial filtering is be applied that projects the signals from the sensor space into components in a source space of some kind. For each component the filter combines electrode signals in a weighted sum. This multivariate approach usually outperforms feature selection by channel picking. The spatial filter can be created implicitly by training a classifier in a supervised way and extracting the spatial weights. Alternatively, a supervised spatial filtering method like Common Spatial Patterns (CSP) can be used to explicitly find the class relevant filters. A spatial filter can also be created in an unsupervised way by restricting the sources to have particular properties. Examples are maximizing statistical independence as in Independent Component Analysis (ICA), or deriving specific spatial locations in the brain as in beam-forming.

When the signal and noise properties are unknown, temporal averaging is commonly used to estimate and time-locked stimulus dependent response. By averaging the noise is canceled under the assumption that the signal and noise are not correlated. If we assume that the signal and noise are also spatially uncorrelated, then spatial averaging (or spatial filtering) can be used in a similar way to cancel out noise. This is the basis for beam-forming when the spatial location of the signal source is known. When the spatial location of the signal is unknown the spatial filter must be estimated form the data. Here we use Canonical Correlation Analysis (CCA) for this purpose. Loosely, this works by estimating a spatial filter, which spatially averages each single-trial time-point to estimate a source signal strength. This source signal strength is as close as possible to the signal strength estimated for the same time-point when temporally averaging all trials. CCA does this by deriving two spatial filters, one for the single-trials (to estimate the single-trial strength) and one for the Event Related Potential (ERP, to estimate the average strength).

Figure 4:
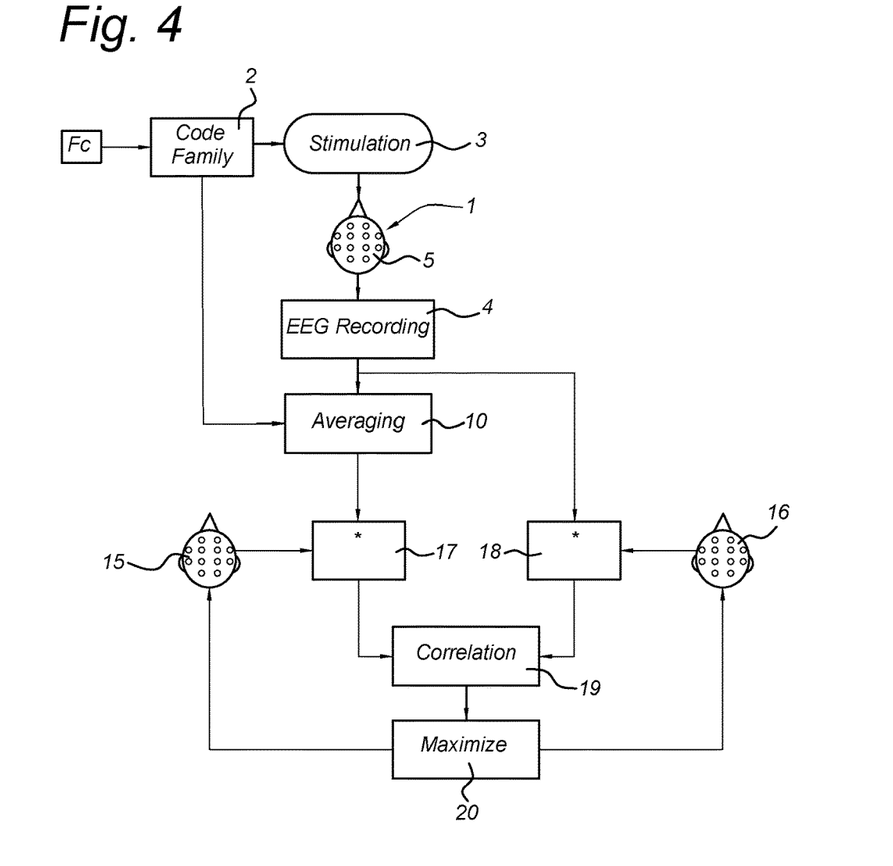
FIG. 4 shows a schematic view of signal processing as applied in the present invention embodiments, for the spatial filtering part thereof.

FIG. 4 shows a schematic diagram of an exemplary CCA pipeline. The stimuli (block stimulation 3) are presented to the user 1 with a clock rate Fc (arrow) fed to a code family (block 2), e.g. the Platinum pick as described above. The detected signals (using detector 5) have the form of an EEG recording 4. The pseudo-random noise sequences are time locked to an averaging block 10, in order to provide the ERP.

Canonical Correlation Analysis optimizes two spatial filters 15, 16. One of these filters, the template filter 15, is applied to the templates (i.e., averaged EEG data (an event related potential, ERP) and one, the trial filter 16, to the single trials, to obtain the respective components 17, 18. A correlation can be computed by concatenating the single-trials and concatenating their corresponding ERPs. The filters 15, 16 which yield the maximum correlation are obtained as the spatial filters 15, 16, using the correlation calculation block 19 and maximize block 20 in a feedback configuration as shown. Thus spatial filtering is applied during training of a classifier to obtain a template filter and a trial filter.

Figure 5:
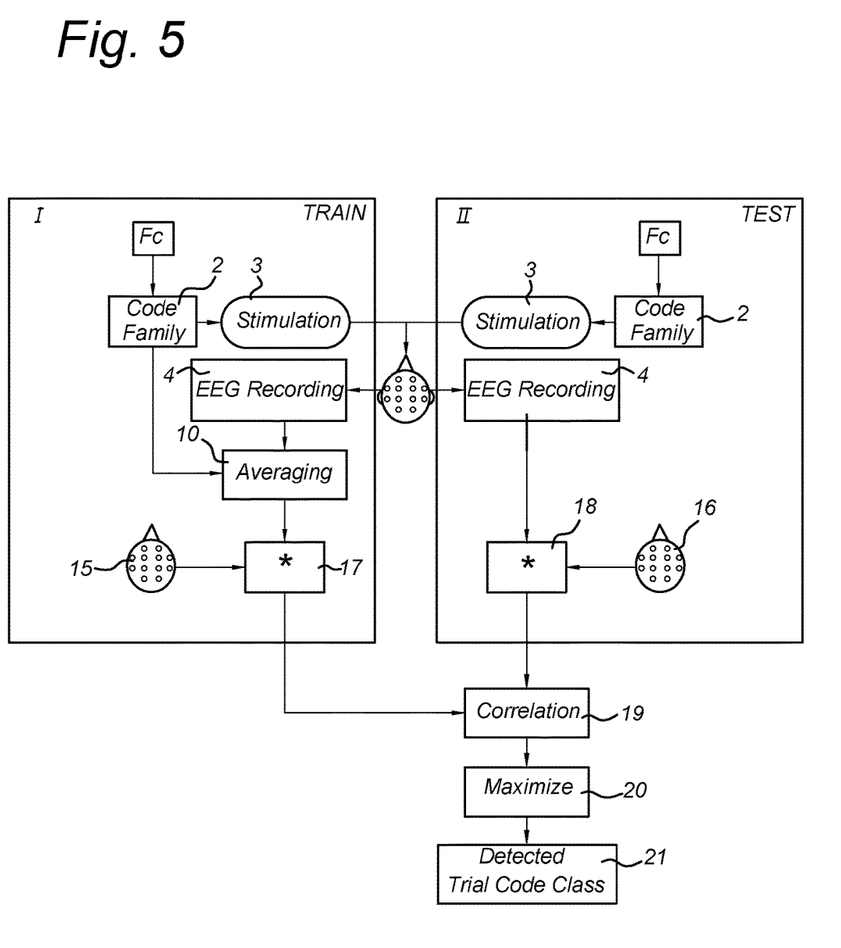
FIG. 5 shows a schematic view of signal processing as applied in the present invention embodiments, for the template matching and spatial filtering part thereof.

If ERPs per class of stimuli can be created from the training data, they can function as template filter 15 to match new unknown single-trials. The best fitting template, using some sort of similarity measure, is chosen as coming from the class that best resembles the single-trial to be classified. As we use CCA to derive an optimized spatial filter that maximizes the correlation between component ERP and component single trial, it is natural to use correlation as similarity measure as well. Thus the classification process becomes parameter-less and is very simple even for a large number of classes. The template matching classifier is then defined as follows:

$$c = \arg\max_i \frac{x^T T_i}{\sqrt{x^T x T_i^T T_i}}$$

where c is the detected class, x is the spatially filtered single-trial (time by 1) and $T_i$ the spatially-filtered template of class i (time by classes). Note that this formula actually resembles the cosine similarity measures. However, because both the single trials and templates are zero-mean (i.e., because of pre-processing), we can use this shorter notation. An illustration of the train and test phase of the template matching classifier is depicted schematically in FIG. 5, which both use the clock rate Fc (arrows to code family block 2). The template matching classifier is defined by spatially filtering the averaged EEG signals of all classes (i.e., the ERPs). Then, during the test phase (using right side of the schematic view of FIG. 5) a single-trial is spatially filtered, and can then be correlated with all classes (correlation block 19). This procedure gives an array of correlation values for each class that tells how well each template fits the single-trial. The template that most resembles the single-trial (using maximize block 20) yields the class label of this trial (Detected trail code class 21).

Because a template matching classifier is used in the present invention embodiments of the BCI method, the templates 15 (i.e., spatially filtered stimulus specific ERPs) will need to be defined, one for each single stimulus that is used in the speller. Normally, a template is generated by building an ERP: averaging over multiple trials of the same stimulus. This has to be repeated for each class and hence requires long training sessions. Instead a further method embodiment of the present invention only requires a few trials and is able to predict templates of stimuli for which no training data was collected. The fact that the bit-sequences used are built as a sequence of pulses is exploited. Assuming linearity of the brain in processing these stimuli, the response to a stimulus sequence can be found by convolution: adding time shifted versions of the pulse response. Usually, in convolution of continuous signals, a Dirac delta pulse (approaching zero duration and infinite amplitude) and its time-shifted, amplified, impulse response is used. A response to a boxcar function is an equally good basis in this case. Because bit-sequences are used that have series of (a few) fixed duration pulses (long pulse and short pulse), the response to each such pulse can be used to predict the response to the whole sequence—under the assumption of a linear system. Conversely, the response to one pulse can be found via linear regression. We can do so given the full response to the whole sequence, and a matrix that describes the structure of the response as composed of time shifted summation of pulse responses (i.e., the structure matrix). If this model explains the responses well, it can be used to generate responses to not-yet seen stimuli. This reduces data collection needed to train the classifier—especially when a large number of classes is needed—like for a matrix speller. As will be explained later, the modulated Gold codes all have two pulses (a short and a long one), hence the analysis and synthesis of responses needs to take into account two different pulse responses, as shown in FIGS. 6a and 6b.

Figure 6A:
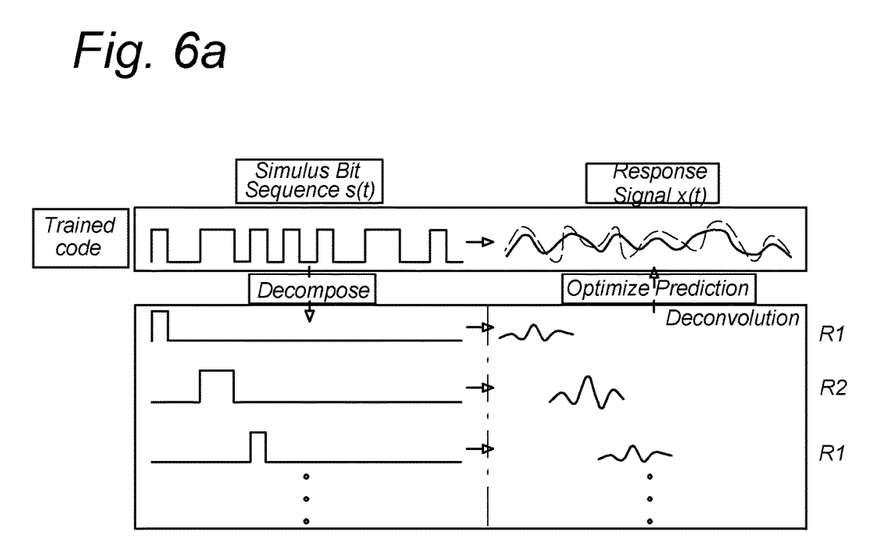
FIGS. 6a and b show waveforms and processing of waveforms as applied in the present invention embodiments, for the re-convolution part thereof.
Figure 6B:
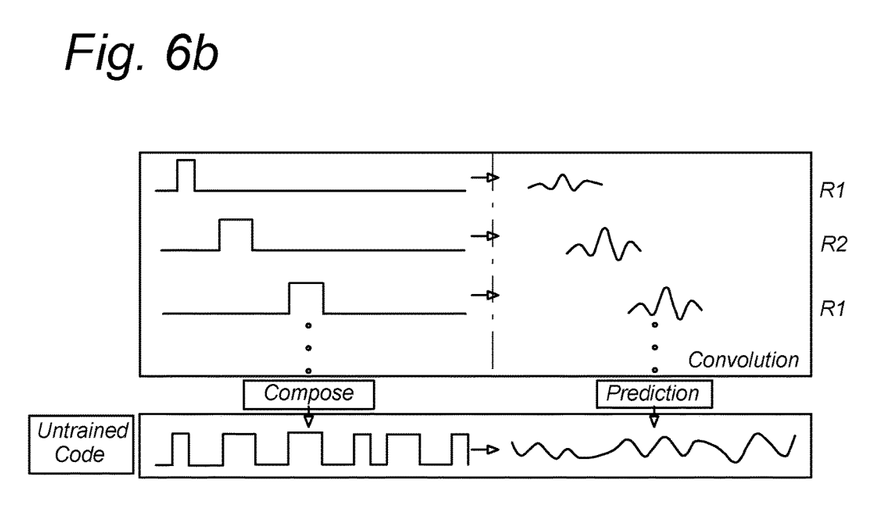

Re-convolution is outlined graphically in the representations as shown in FIGS. 6a and 6b. The train sequence 11 is decomposed into its parts, which comprises short and long pulses. The responses R1, R2 to those pulses are optimized (by linear regression) to predict the overall response (Response signal x(t)), as shown in FIG. 6a. Then, given this model works well, summing the time-shifted versions of the derived pulse responses R1, R2 according to an untrained sequence predicts the response, as shown in FIG. 6b. Thus, in the method embodiments, processing the detected brain wave signal may comprise template matching with templates predicted by applying re-convolution processing.

In the present exemplary embodiments, the decomposition is based on long (1100) and short pulses (10). The model of decomposition can be written as:

$$x(t) = \sum_{i=1}^{N} \sum_{\tau=1}^{L_i} I_i(t) R_i(t - \tau)$$

where x(t) is the response at time t, N is the number of events (i.e., the different pulse responses), $L_i$ is the duration of event i, $R_i$ is the response on the $i^{th}$ event, and $I_i$ is the indicator function that is 1 if the $i^{th}$ event happens at time t and 0 otherwise. To build the design matrix a Toeplitz structure is used, that lists the events at each point in time. The model is then expressed as:

$$x(t) = \begin{bmatrix} \vdots & \cdots & \vdots \\ I_1(t\!:\!t+L_1) & \cdots & I_N(t\!:\!t+L_N) \\ \vdots & \cdots & \vdots \end{bmatrix} \begin{bmatrix} R_1 \\ \vdots \\ R_N \end{bmatrix} = Mp$$

where x are the modeled responses, M is the decomposition matrix containing events shifted one sample at each row, and p is the concatenation of all the types of pulse responses. In other words, the template prediction may comprise using a response of a first fixed duration pulse and a response of second fixed duration pulse.

Figure 7:
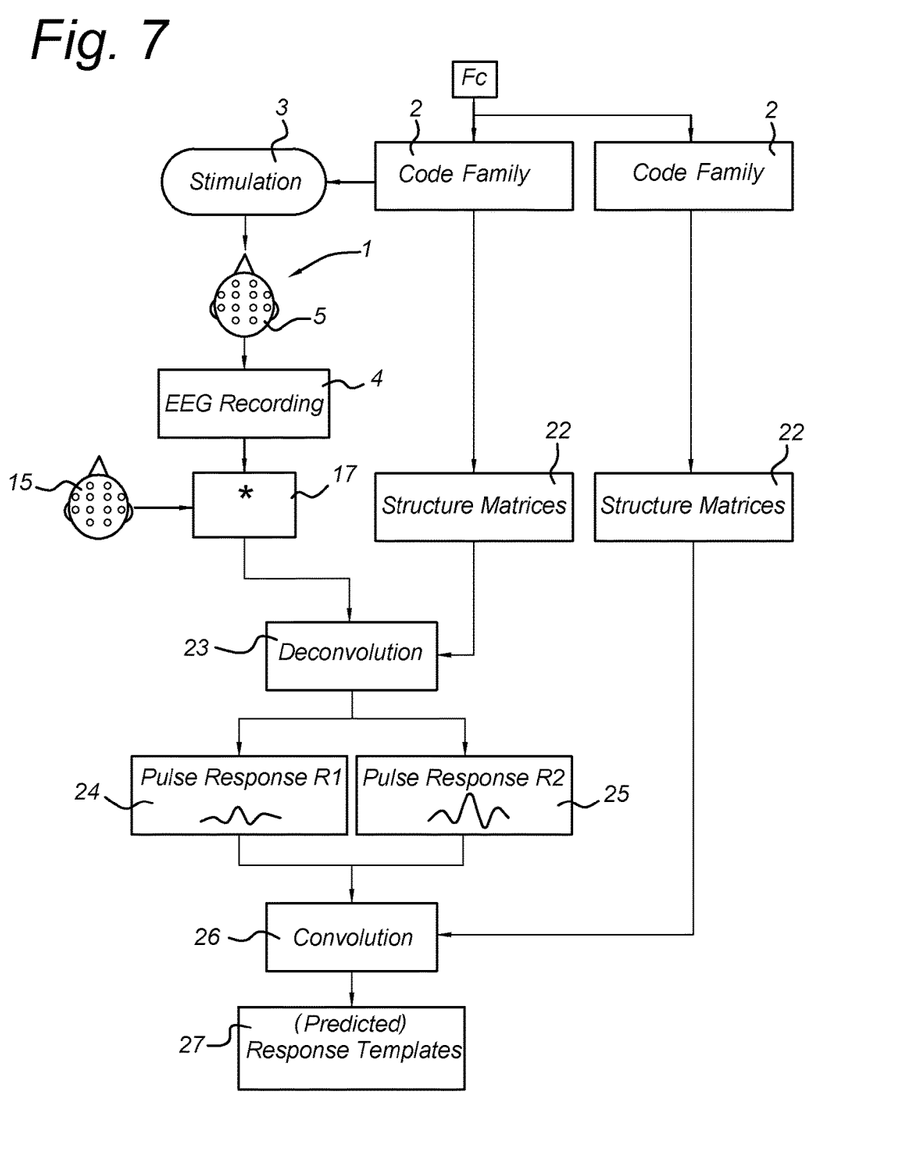
FIG. 7 shows a schematic view of the re-convolution pipeline as part of the processing as applies in the present invention embodiments.

The above is also shown schematically in the processing pipeline as depicted in FIG. 7. Again, using a clock frequency Fc a specific pseudo-random noise sequence out of the code family 2 is selected and used as stimulation 3. An EEG recording 4 is obtained from the test person 1 using the detector 5, and the template filter 15 is applied for processing in block 17.

From the code family 2, structure matrices 22 are derived as discussed above, and one is used for the de-convolution step 23. Pulse responses R1 and R2 (for the long and short pulse) 24, 25 are obtained, and used together with the structure matrix 22 as input for the subsequent convolution step 26, which results in the (predicted) response templates 27.

When enough training data is available, one can determine a fixed time interval needed for a desired classifier performance. One could also define a criterion to dynamically decide when trials can be stopped and the classification decision can be emitted. In online processing of test data, the window of a single-trial is sequentially increased as long as the classifier produces a criterion value below the required cut-off level. If the classifier is certain enough, trial window increment stops and the classifier emits its output. This approach provides a possible speed gain and an easy adaptation to occasional distractions and 'bad' trials.

According to the present invention the maximum correlation (i.e. the correlation with the best matching template), or the correlation margin (i.e., the difference in correlation between best and second best matching templates) can be used in further embodiments as indication that a decision on the best matching template can be made reliably (i.e. it is the correct answer with high enough probability). To arrive at a sensible cut-off criterion for these measures an analysis can be made of their evolving distributions, conditioned on the correctness of outcome at the time. This then dictates a proper cut-off value that will result in the desired performance level. Histograms of criteria evolve over time and at each point the stop criterion may be checked by lowering the criterion until the performance is reached. Note that for a correct analysis it has to model the dynamic nature of this process and exclude already stopped trials from next steps in the analysis.

In the present invention embodiments as described above, a way was presented to watermark (visual) stimuli with so called noise tags (pseudo random bit-sequences), and detected their responses in EEG. For stimuli families of special codes, Gold codes, were used that exhibit preferable correlation properties. The codes were modulated to limit their low frequency content, which also translates them into a sequence that can additionally be considered a concatenation of only two basic pulse shapes, a short and a long one. The dimensionality of responses was reduced by Canonical Correlation Analysis, substituting part of the noise reduction that usually is achieved by averaging repeated single-trials in an ERP by a weighted spatial averaging. This signal is de-convolved into responses to the two pulse shapes that make up the stimuli. The resulting pulse responses were re-convolved into predicted responses for the whole family of codes. These formed the templates of the template matching classifier, which simply chooses the label of the template with highest correlation with the single-trial response. Because the family of codes is potentially larger than the needed number of classes, a cross-correlation matrix of the predicted templates was used to select a subset which could be best distinguished from each other. The codes in the subset were then allocated optimally to cells in the 6 by 6 speller matrix to minimize crosstalk from neighboring cells. The training data was sliced into small time intervals and an early stopping criterion was derived based on the margin between the best and second best correlation between single-trials and templates.

The BCI setup was tested in an online experiment involving two conditions: fixed length trials and early stopping. In both conditions a performance of 86% was achieved. However, in terms of communication rates early stopping was substantially faster (30% on average). This effect can be explained by early stopping having the advantage of stopping trials once the method is confident, resulting in shorter trial lengths. Secondly, and maybe more important, early stopping has the advantage of increasing the trial length if there is uncertainty, giving more information to the algorithm yielding higher performances. As such, 'adaptive stopping' might be a better name for that method embodiment.

The availability of a generative model makes it possible to use a short calibration (training) session, but also to optimize and predict the performance of specific BCI setup without testing all stimulus sequences, which is a great advantage. The CCA and the de-convolution yield interesting spatio-temporal patterns of pulse responses that were very similar across subjects. Here the method can even contribute to a better understanding of the neuronal basis of the responses to non-periodic signals: Broad Band Evoked Potentials.

A few practical applications have been developed and have been used in to demonstrate system feasibility. One of these replicates the can-toss game. In this game participants only have to look at cans to make the cans to fall down.

Also, the speed of communication is improved by making the pipeline asynchronous. More specifically, the modulated Gold codes only show high correlation for auto-correlation at time lag 0. This means we do not need to know the exact time of stimulation. This allows to move to an asynchronous BCI based on continuous stimulation. This has usability advantages by means of the user being allowed to look at a character at any time to select it. In addition, it has advantages for artifact rejection as the system can simply ignore data corrupted by any noise source and start analyzing whenever the data is clean again. In short, an asynchronous BCI speller would keep on stimulating, which as a result minimizes the ITI and optimizes CR, hence maximizes the ITR. Thus, in a further embodiment of the present invention, the one or more stimuli are applied continuously.

To summarize, the importance and performance of a Broad Band Evoked Potential based Brain Computer Interface has been shown. More specifically, using a generative model, it was possible to predict responses and hence optimize stimulation properties such as code subsets and layout allocations. All together the proposed pipeline optimized communication rates up to 201.35 bits per minute (38.95 characters per minute) for the best participant.

The present invention embodiments have been described above with reference to a number of exemplary embodiments as shown in the drawings. Modifications and alternative implementations of some parts or elements are possible, and are included in the scope of protection as defined in the appended claims.

The invention claimed is:

1. A method for processing a brain wave signal obtained from a person using a brain wave detector, comprising:
   applying one or more stimuli to the person in which each of the one or more stimuli comprises a pseudo random noise component modulating the stimulus intensity;
   detecting a brain wave signal after applying the one or more stimuli; and
   processing the detected brain wave signal to calculate which of the one or more stimuli is present in the detected brain wave signal using correlation techniques,
   wherein the pseudo random noise component comprises a pseudo random noise sequence of the class of maximum length sequences, which are further modulated with twice their associated bit frequency.

2. The method according to claim 1, wherein the class of maximum length sequences comprise Gold code sequences.

3. The method according to claim 1, wherein the pseudo random noise component is one of an optimized set of pseudo random noise sequences, wherein the optimized set is obtained using cross correlation and auto correlation parameters of the associated predicted brain responses.

4. The method according to claim 3, wherein the optimized set is obtained by first clustering the set of pseudo random noise codes, and providing the optimized set by selecting one pseudo random noise sequence from each cluster.

5. The method according to claim 3, wherein the optimized set is provided using an iterative process, wherein each cluster is subsequently reduced to a single pseudo random noise sequence.

6. The method according to claim 3, wherein the pseudo random noise sequences of the optimized set are allocated to a position in a two-dimensional matrix, wherein cross-talk between neighboring cells in the two-dimensional matrix is minimized.

7. The method according to claim 1, wherein processing the detected brain wave signal comprises spatial filtering and classification by template matching.

8. The method according to claim 7, wherein spatial filtering is applied during training of a classifier to obtain a template filter and a trial filter.

9. The method according to claim 1, wherein processing the detected brain wave signal comprises template matching with templates predicted by applying re-convolution processing.

10. The method according to claim 9, wherein the template prediction comprises using a response of a first fixed duration pulse and a response of second fixed duration pulse.

11. The method according to claim 1, wherein the one or more stimuli are applied continuously.

12. A brain computer interface comprising
    a stimulator for applying stimuli to a person,
    a detector for obtaining a brain wave signal from the person,
    a processor connected to the detector and arranged to process the brain wave signal according to claim 1, and
    a device connected to the processor (6) and arranged to receive processed data from the processor.

13. A non-transitory computer-readable medium comprising computer executable code, which when loaded on a computer system connected to a stimulator for applying stimuli to a person and to a detector arranged to receive data associated with a brain wave signal, provides the computer system with the functionality to perform the steps of:
    applying one or more stimuli to the person in which each of the one or more stimuli comprises a pseudo random noise component modulating the stimulus intensity;
    detecting a brain wave signal after applying the one or more stimuli; and
    processing the detected brain wave signal to calculate which of the one or more stimuli is present in the detected brain wave signal using correlation techniques,
    wherein the pseudo random noise component comprises a pseudo random noise sequence of the class of maximum length sequences, which are further modulated with twice their associated bit frequency.

* * * * *